US00PP15017P2

(12) United States Plant Patent
Olesen et al.

(10) Patent No.: US PP15,017 P2
(45) Date of Patent: Jul. 13, 2004

(54) MINIATURE ROSE PLANT NAMED 'POULRA024'

(50) Latin Name: *Rosa hybrida*
Varietal Denomination: POULra024

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/673,106

(22) Filed: Sep. 25, 2003

(51) Int. Cl.[7] ..... A01H 5/00
(52) U.S. Cl. ..... Plt./121
(58) Field of Search ..... Plt./121, 116, 128

*Primary Examiner*—Bruce R. Campell
*Assistant Examiner*—June Hwu

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULra024'.

SUMMARY OF THE INVENTION

The present discovery constitutes a new and distinct variety of a miniature pot rose plant which was discovered in a cultivated area. The mutation resulted from 'POULra002', a miniature pot rose hybridized by the same inventors. 'POULra002' is described and illustrated in U.S. Plant Pat. No. 13,275, and issued on Nov. 26, 2002. The new rose variety resulted from a naturally occurring mutation of unknown causation on a branch of 'POULra002'.

The rose plant of the present discovery has a unique combination of charateristics which are outstanding in the new variety and which distinguish it from the original rose 'POULra002' as well as all other varieties which we are aware of. For example, the new variety has:

1. Uniform and abundant pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra024' from all other varieties of which we are aware.

The resulting mutation was selected and evaluations were conducted on the resulting rose plants in a controlled environment.

Asexual reproduction of 'POULra024' by cuttings and traditional budding was first done by L. Pernille and Mogens N. Olesen in their nursery in Fredensborg, Denmark in 1998. This initial and other subsequent propagations conducted in controlled environments have demonstrated that the characteristics of 'POULra024' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra024'. Specifically illustrated in FIG. 1:

FIG. 1.1; Stem showing the attachment of leaves, peduncle, and open flower;

FIG. 1.2; Flower bud closed, partially opened, and ¼ open;

FIG. 1.3; Sepals, receptacle, and pedicel, and reproductive organs;

FIG. 1.4; Flower petals, detached;

FIG. 1.5; Mature and juvenile leaves;

FIG. 1.6; Bare stem with thorns.

DETAILED DESCRIPTION OF THE VARIETY

The following is a description of 'POULra024', as observed in its growth in glasshouses in Burlington, Ontario. Plants were grown in 10.5 cm pots, for a duration of 10 weeks. Color references are made using The Royal Horticultural Society (London, England) Colour Chart, 1995, except where common terms of color are used.

For a comparison, several physical characteristics of the rose variety 'POULra002', a rose variety from the same inventors described and illustrated in U.S. Plant Pat. No. 13,275 issued on Nov. 26, 2002, are compared to 'POULra024' in Chart 1.

CHART 1

| | 'POULra024' | 'POULra002' |
|---|---|---|
| Flower Diameter when open. | 45–50 mm. | 35–45 mm. |
| Petal Count | 31 under normal conditions. | 35–45 under normal conditions. |
| Flower Bud Color as Sepals unfold. | Red Group 53C. Red Group 53C to 52B at ¼ opening. | Red Group 47B. Red Group 50A at ¼ opening. |

FLOWER AND FLOWER BUD

Blooming habit: Continuous.

Flower bud:

*Size.*—Upon opening, 29 mm in length from base of receptacle to end of bud by 11 mm in width.

*Bud form.*—Pointed ovoid.

*Bud color.*—As sepals unfold, petals are Red Group 53C. Red Group 53C to 52B at ¼ opening.

*Sepals.*—Color: Upper Surface is Green Group 137A. Anthocyanin observed in medium amount. Greyed-Purple Group 183A at sepal apex. Lower Surface is Yellow-Green Group 146B. Observations: Medium foliaceous appendages on three of the five sepals. Surfaces of sepals slightly pubescent. Stipitate glands are scant. Shape: Sepal apex is cirrhose. Base is flat at union with receptacle. Size: 22 mm long×7 mm wide.

*Receptacle.*—Surface: Smooth and very lightly pubescent. Shape: Urn shaped. Size: 7 mm (h)×7 mm (w). Color: Yellow-Green Group 144B.

*Peduncle.*—Surface: Smooth and stipitate glands medium. Length: 55 mm average length. Color: Yellow-Green Group 144B. Strength: Strong to somewhat strong.

*Borne.*—Multiples of 1 to 2 buds per flowering stem.

Flower bloom:

*Fragrance.*—Light.

*Duration.*—The blooms have a duration on the plant of approximately 10 to 14 days. Petals fall cleanly away from plant.

*Size.*—Medium for a 10.5 cm pot rose. Average flower diameter is 45 mm to 50 mm when open. Average flower depth is 20 mm when open.

*Form.*—Double. Shape of flower when viewed from the side: Upon opening, upper part: Flat. Upon opening, lower part: Flattened convex. Open flower, upper part: Flattened convex. Open flower, lower part: Flattened convex.

*Petalage.*—Double 20 to 40. Average range: 31 petals under normal conditions with 3 to 4 petaloids.

Color:

*Upon opening, petals.*—Outermost petals: Outer Side: Red-Purple Group 58B. Inner Side: Red Group 52C. Innermost petals: Outer Side: Red-Purple Group 58B. Inner Side: Red Group 52C.

*Upon opening, basal petal spots.*—Outermost petals: Outer Side: White Group 155A. Inner Side: White Group 155A. Innermost petals: Outer Side: White Group 155A. Inner Side: White Group 155A.

*After opening, petals.*—Outermost petals: Outer Side: Red-Purple Group 58B. Inner Side: Red Group 52C. Innermost petals: Outer Side: Red-Purple Group 58B. Inner Side: Red Group 52C.

*After opening, basal petal spots.*—Outermost petals: Outer Side: White Group 155A. Inner Side: White Group 155A. Innermost petals: Outer Side: White Group 155A. Inner Side: White Group 155A.

General tonality: On open flower Red Group 52C. No change in the general tonality at the end of the $7^{th}$ day. Afterwards, general tonality is Red Group 52C.

Petals:

*Petal reflex.*—Somewhat.

*Petal edge.*—Entire.

*Shape.*—Base shape is round, to somewhat accute. Apex shape is round, with point in center of margin.

*Petaloids.*—Quantity: 10. Shape: Very acute base and rounded apex. Size: 7 mm long; 4 mm wide. Color: Outer side is Red Purple 58B. Inner Side is Red Purple 52C.

*Thickness.*—Average.

*Texture.*—Smooth.

*Arrangement.*—Not formal.

Reproductive organs:

*Pollen.*—None observed.

*Pistils.*—Length: 3 mm long. Quantity: 30 actual count.

*Anthers.*—Size: 3 mm long. Color: Greyed-Yellow Group 162A. Quantity: 43 actual count.

*Filaments.*—Color: Yellow Group 6C. Length: 4 mm.

*Stigmas.*—Inferior in relation to anthers. Color: Green-Yellow Group 160C.

*Styles.*—Color: Red Group 50B.

*Seed formation.*—Hips not observed.

PLANT

Plant growth: Moderate, compact, upright to bushy. When grown as a 10.5 cm pot plant, the average height of the plant itself is 25 cm and the average width is 18 cm.

Stems:

*Color.*—Young wood: Yellow-Green Group 146B. Older wood: Yellow-Green Group 146B.

*Thorns.*—Incidence: 3 thorns per 10 cm of stem on average. Size: 4 to 5 mm in length. Color: Greyed-Yellow Group 160C. Shape: Linear.

*Size.*—Average length: 15 cm from flower to first branch. Stem diameter is 3 mm.

*Internodal distance.*—43 mm (average.) Shape: Concave.

*Surface.*—Young wood: Smooth. Older wood: Smooth.

Plant foliage: Normal number of leaflets on normal leaves in middle of the stem: 5 to 7 leaflets.

*Compound leaf size.*—90 mm (l)×52 mm (w).

*Quantity.*—1 leaf per 43 mm of stem.

*Color.*—Mature foliage: Upper Leaf Surface: Green Group 137A. Lower Leaf Surface: Green Group 138B. Juvenile foliage: Upper Leaf Surface: Green Group 137A. Lower Leaf Surface: Green Group 138B. Anthocyanin intonation: Yes. Location: Margins of juvenile foliage. Color: Grey-Purple Group 183A.

Plant leaves and leaflets:

*Stipules.*—Size: 10 mm. Color: Green Group 138A. Presence of stipitate glands: Medium.

*Petiole.*—Length: 15 mm. Width: 1 mm. Color: Yellow-Green Group 144A. Underneath: Thorns and stipitate glands. Anthocyanin: Green-Purple Group 183A.

*Rachis.*—Length: 26 mm. Color: Yellow-Green Group 144A. Underneath: Thorns and stipitate glands observed. Anthocyanin: Green-Purple Group 183A.

*Leaflet.*—Edge: Finely serrated. Shape: The general shape is Elliptical to Ovate. The apex is acute. The base is rounded. Texture: Smooth. Arrangement: Odd pinnate. Venation: Reticulate. Leaf Gloss: Matte Finish. Size: 32 mm (l)×21 mm (w).

Disease resistance: Average resistance to mildew, black spot, and Botrytis under normal growing conditions in Burlington, Canada.

What is claimed:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

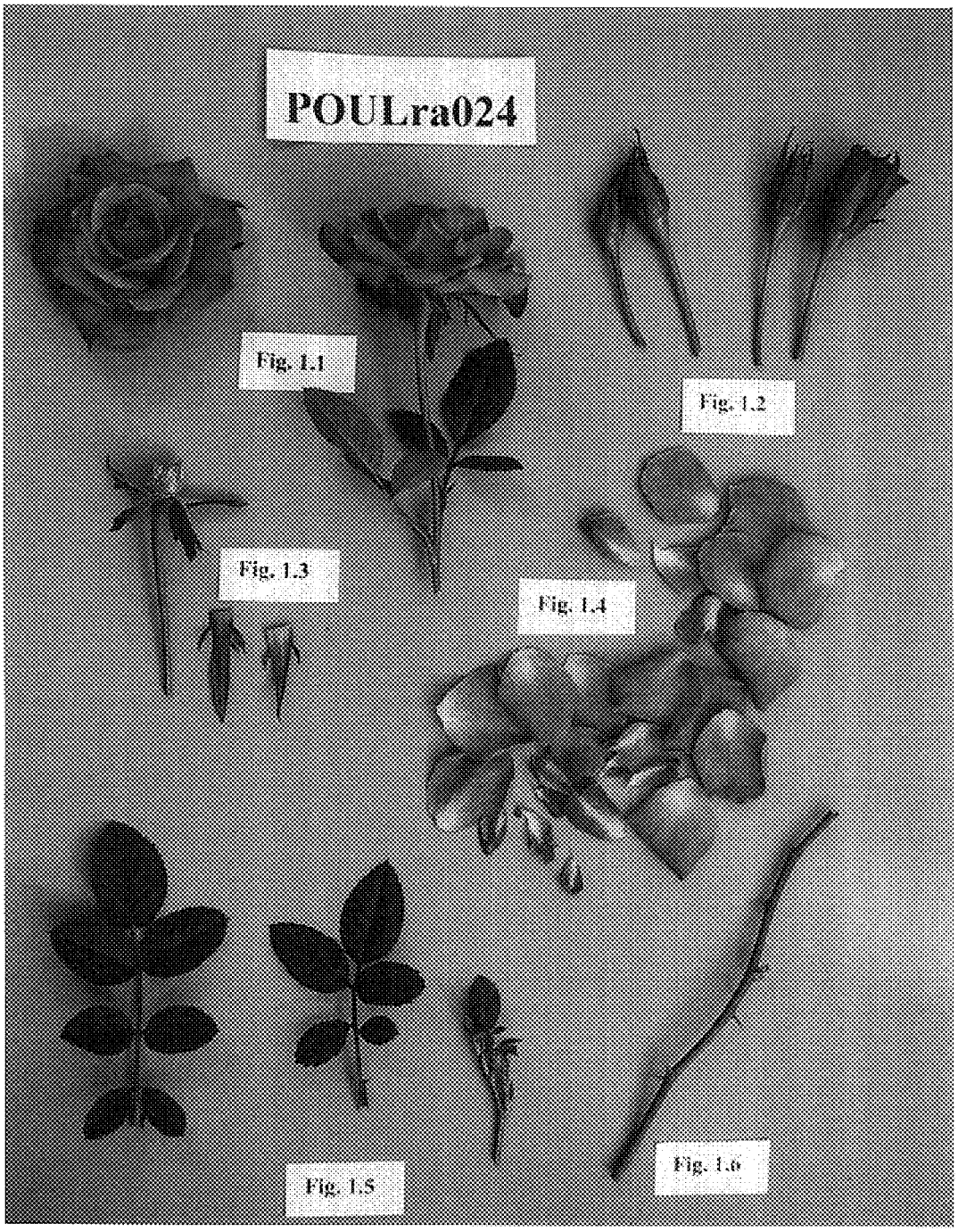
POULra024
Fig. 1.1
Fig. 1.2
Fig. 1.3
Fig. 1.4
Fig. 1.5
Fig. 1.6